US011890324B2

(12) United States Patent
Sams Nielsen et al.

(10) Patent No.: US 11,890,324 B2
(45) Date of Patent: Feb. 6, 2024

(54) COMPOUNDS FOR USE IN INDUCING MYOCARDIAL PERFUSION RECOVERY

(71) Applicant: Epoqe Pharma ApS, Copenhagen N (DK)

(72) Inventors: Anette Sams Nielsen, Kgs. Lyngby (DK); Lars Ingvar Herbert Edvinsson, Lund (SE)

(73) Assignee: Epoqe Pharma ApS, Copenhagen N (DK)

( * ) Notice: Subject to any disclaimer, the term of this patent is extended or adjusted under 35 U.S.C. 154(b) by 24 days.

(21) Appl. No.: 17/309,720

(22) PCT Filed: Dec. 20, 2019

(86) PCT No.: PCT/SE2019/051333
§ 371 (c)(1),
(2) Date: Jun. 16, 2021

(87) PCT Pub. No.: WO2020/130927
PCT Pub. Date: Jun. 25, 2020

(65) Prior Publication Data
US 2022/0031809 A1 Feb. 3, 2022

(30) Foreign Application Priority Data
Dec. 21, 2018 (SE) .................... 1851652-6

(51) Int. Cl.
*A61K 38/00* (2006.01)
*A61P 9/08* (2006.01)
*A61P 9/00* (2006.01)
*A61P 9/10* (2006.01)
*A61K 38/22* (2006.01)
*A61K 45/06* (2006.01)

(52) U.S. Cl.
CPC ............ *A61K 38/225* (2013.01); *A61K 45/06* (2013.01); *A61P 9/08* (2018.01)

(58) Field of Classification Search
CPC . A61K 38/225; A61P 9/08; A61P 9/00; A61P 9/10
See application file for complete search history.

(56) References Cited

U.S. PATENT DOCUMENTS

2009/0023643 A1* 1/2009 Southard ................ A61K 38/17
514/6.9

FOREIGN PATENT DOCUMENTS

| WO | WO2005/067890 | 7/2005 |
| WO | 2005/070445 | 8/2005 |
| WO | WO2005/070444 | 8/2005 |
| WO | 2009/142727 | 11/2009 |
| WO | 2011/051312 | 5/2011 |

OTHER PUBLICATIONS

Dai et al., "Clinical Use of Aspirin in Treatment and Prevention of Cardiovascular Disease," Thrombosis, 2011, 2012: 1-7. (Year: 2011).*
International Search Report dated Feb. 7, 2020 in PCT/SE2019/051333.
Written Opinion dated Feb. 7, 2020 in PCT/SE2019/051333.
Swedish Search Report dated Jul. 5, 2019 in Swedish Application No. 1851652-6.
Aubdool et al., "*A Novel α-Calcitonin Gene-Related Peptide Analogue Protects Against End-Organ Damage in Experimental Hypertension, Cardiac Hypertrophy, and Heart Failure*," Circulation, 2017; 136:367-383.
Kee et al., "*The Role of Calcitonin Gene Related Peptide (CGRP) in Neurogenic Vasodilation and Its Cardioprotective Effects*," Front. Physiol. 9:1249, Sep. 2018, pp. 1-13.
Sheykhzade et al., "*Vascular and molecular pharmacology of the metabolically stable CGRP analogue, SAX*," European Journal of Pharmacology 829 (2018) 85-92.
International Preliminary Report on Patentability dated Jan. 20, 2021 in PCT/SE2019/051333, 7 pages.
Bentsen et al., "Myocardial perfusion recovery induced by an α-calcitonin gene-related peptide analogue", Journal of Nuclear Cardiology, Jun. 4, 2021, 10 pages.
Källner et al., "Calcitonin gene-related peptide in myocardial ischaemia and reperfusion in the pig", Cardiovascular Research, vol. 38, 1998, pp. 493-499.
Lewis C. Becker, "Conditions for Vasodilator-induced Coronary Steal in Experimental Myocardial Ischemia", vol. 57, No. 6, Jun. 1978, pp. 1103-1110.
Nilsson et al., "Long acting analogue of the calcitonin gene-related peptide induces positive metabolic effects and secretion of the glucagon-like peptide-1", European Journal of Pharmacology, vol. 773, 2016, pp. 24-31.
Russell et al., "Calcitonin Gene-Related Peptide: Physiology and Pathophysiology", Physiol. Rev., vol. 94, 2014, pp. 1099-1142.
Sams et al., "Equipotent in vitro actions of α- and ß-CGRP on guinea pig basilar artery are likely to be mediated via CRLR derived CGRP receptors", Regulatory Peptides, vol. 85, 1999, pp. 67-75.

(Continued)

*Primary Examiner* — Julie Ha
(74) *Attorney, Agent, or Firm* — Grüneberg and Myers PLLC (57) ABSTRACT

A calcitonin gene-related peptide (CGRP) compound can be selected from N-alpha-[2-(2-{2-[(S)-4-carboxy-4-(17-carboxyheptadecanoylamino)-butyrylamino]ethoxy}ethoxy) acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyrylamino]-ethoxy}ethoxy)acetyl][Ser1]beta-human CGRP peptide (β-CGRP-analogue), or derivatives thereof. The CGRP compound can be used to induce myocardial perfusion recovery, in connection with AMI, by activating any CGRP family of receptors with a larger CGRP compound: CGRP potency ratio in the coronary artery than in the mesenteric artery.

15 Claims, 5 Drawing Sheets
Specification includes a Sequence Listing.

(56) References Cited

OTHER PUBLICATIONS

Sheykhzade et al., "Homologous desensitization of calcitonin gene-related peptide-induced relaxation in rat intramural coronary arteries", European Journal of Pharmacology, vol. 484, 2004, pp. 91-101.

Sohn et al., "The effects of CGRP in vascular tissue—Classical vasodilation, shadowed effects and systemic dilemmas", European Journal of Pharmacology, vol. 881, No. 173205, 2020, pp. 1-12.

* cited by examiner

COMPOUNDS FOR USE IN INDUCING MYOCARDIAL PERFUSION RECOVERY

CROSS-REFERENCE TO RELATED APPLICATIONS

This application is the National Stage entry under § 371 of International Application No. PCT/SE2019/051333, filed on Dec. 20, 2019, and which claims the benefit of priority to Swedish Application No. 1851652-6, filed on Dec. 21, 2018. The content of each of these applications is hereby incorporated by reference in its entirety,

REFERENCE TO A SEQUENCE LISTING

The present application is accompanied by an ASCII text file as a computer readable form containing the sequence listing entitled, "003649USPCT_ST25.txt", created on Jun. 15, 2021, with a file size of 1,372 bytes, the content of which is hereby incorporated by reference in its entirety.

BACKGROUND OF THE INVENTION

The Technical Field of the Invention

The present invention is related to a calcitonin gene-related peptide (CGRP) compound selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyryl-amino]-ethoxy}ethoxy)acetyl][Ser1]beta-human CGRP peptide (β-CGRP-analogue), or derivatives thereof, for use in inducing myocardial perfusion recovery by activating any CGRP family of receptors.

Description of Related Art

The most serious cardiovascular diseases is the myocardial infarction (MI) such as acute myocardial infarction (AMI). It is responsible for over 15% of mortality each year. The risk factors such as dyslipidemia, smoking, psychosocial stressors, diabetes mellitus, hypertension, obesity, alcohol consumption, physical inactivity, and a diet low in vegetables have been strongly associated with the risk of acute MI. There is a continuous priority to increase the survival rate of these patients.

There is also continuous activity to reduce the time of hospitalization and improve the chance of recovery to normal life, aspects which are important from the perspective of society, both in short term but also in long term. For example, in view of high costs for rehabilitation, reduced disability and reduced need for individual care and support to return to normal life, etc. Calcitonin gene-related peptide (CGRP) is one of the most potent vasodilators known and the structure and actions of CGRP are highly conserved within mammalian species.

The classical and most well characterized action of CGRP is CGRP-receptor induced vasodilation. Although molecular CGRP-receptors (CRLR and RAMP1) and CGRP-IR have been demonstrated in both vascular smooth muscle and endothelium, mainly endothelium-independent vasodilation has been shown in various vascular beds.

The endogenous physiological source of CGRP is perivascular sensory nerve terminals where CGRP-release is stimulated by e.g. vanniloid receptor agonists (such as capsaicin) or by depolarization that triggers calcium-dependent endocytosis. Endogenous CGRP is a protective substance in neuronal and vascular crisis inducing a compensatory local vasodilatory effect to severe vasoconstriction.

Endogenous CGRP has repeatedly been associated to preconditioning-induced cardio protection during experimental myocardial infarct reperfusion damage. The CGRP-mediated protection from reperfusion damage has been observed in preconditioning by brief coronary occlusion, heat stress, remote (mesenteric) occlusion, nitroglycerin, isoproterenol, evodiamine, capsaicin and rutaecarpine.

Importantly, exogenous CGRP has been shown to induce similar cardioprotective effects in isolated hearts whereas cardio protection by exogeneous CGRP is not reproduced in reperfusion studies in vivo. This is most likely due to the fact that CGRP induces peripheral vasodilation that increases the workload on the heart and thereby promotes increased ischemic damage of heart tissue.

Indeed, CGRP has been shown to induce positive chronotropic and ionotropic effects on the isolated guinea pig heart and in isolated human myocardial trabeculae. Further, in clinical studies with CGRP infusion for experimental treatment of cerebral vasospasm, adverse effects of increased heart rate and peripheral hypotension was demonstrated. The increased heart rate and peripheral vasodilation was also the main reason for withdrawal of patients in the CGRP treatment group in a large clinical trial.

These data indeed support basic physiology: that the cardiac need for oxygen will increase during systemic CGRP treatment and thus, the combined information from basic physiology and experimental pharmacology supports that exogeneous CGRP will therefore have a negative effect on myocardial perfusion recovery after acute myocardial infarct (AMI). This is supported by the findings that CGRP has a lower vasodilatory potency in coronary artery than in peripheral and cerebral artery.

Recently, a novel metabolically stable αCGRP analogue, N-alpha-[2-(2-{2-[(S)-4-carboxy-4-(17-carboxyheptadecanoylamino)butyrylamino]ethoxy}-ethoxy)-acetyl][Ser1] alpha-human CGRP peptide, has been invented. The αCGRP analogue is reversing hypertension and complications of hypertension in experimental animals.

U.S. Pat. No. 8,835,379 discloses CGRP compounds, one of which is N-alpha-[2-(2-{2-[(S)-4-carboxy-4-(17-carboxyheptadecanoylamino)butyrylamino]-ethoxy}ethoxy) acetyl][Ser1]alpha-human CGRP peptide (αCGRP analogue).

A method of treating diabetes, insulin resistance, obesity, hypertension and cardiovascular diseases by administering one of the disclosed CGRP compounds is also described.

All previous data indicate that the αCGRP analogue, N-alpha-[2-(2-{2-[(S)-4-carboxy-4-(17-carboxyheptadecanoylamino)butyrylamino]-ethoxy}ethoxy)acetyl][Ser1] alpha-human CGRP peptide, and CGRP display similar pharmacological actions (Sheykhzade, M., et al., Vascular and molecular pharmacology of the metabolically stable CGRP analogue, SAX, Eur. J. Pharmacol. 2018, Jun. 15; 829: 85-92), only is the in vitro potency of αCGRP analogue approximately 10 times lower than that of CGRP, whereas the half-life and molecular size of αCGRP analogue is increased as compared to CGRP (Nilsson, Hansen et al, Long acting analogue of the calcitonin gene-related peptide induces positive metabolic effects and secretion of the glucagon-like peptide-1, European Journal of Pharmacology, 2016, 773, 24-31).

Myocardial infarction (MI), commonly known as a heart attack, occurs when blood flow is reduced or stops to a part of the heart, causing damage to the heart muscle. The complete blockage of a coronary artery caused by a rupture of an atherosclerotic plaque is usually the underlying mechanism of an MI. Treatment of an MI is time-critical. Today, it is known that the damages of the heart increase as time passes from the incident of acute myocardial infarct. For instance, it would be beneficial to treat a patient suffering from AMI as quickly as possible after the incident, for instance during the transport of the patient to the hospital. Annually, the number of incidents worldwide of myocardial in facts has been estimated to 32.4 million. Therefore, there is a demand to improve prognosis and to reduce the time of hospitalization required for these patients.

There is a need within the art to find novel treatments of compromized myocardial perfusion, e.g. acute myocardial infarction, especially shortly after the incidence of the acute myocardial infarction.

SUMMARY OF THE INVENTION

The present invention is related to a new use of calcitonin gene-related peptide (CGRP) receptor agonist, where the new use is that the CGRP receptor agonist causes a reduction in myocardial perfusion defect in experimental acute myocardial infarct.

An aspect of the invention, a calcitonin gene-related peptide (CGRP) compound selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyryl-amino]-ethoxy}ethoxy)acetyl][Ser1]beta-human CGRP peptide (β-CGRP-analogue), or derivatives thereof, for use in inducing coronary perfusion recovery, in connection with acute myocardial infarct, AMI, by activating any CGRP family of receptors with a larger CGRP: CGRP compound potency ratio in coronary artery than in mesenteric artery.

In one embodiment of the CGRP compound for use as defined herein is of human origin.

Another embodiment of the invention is a CGRP compound for use, wherein the myocardial perfusion is compromised and is in connection with a disease selected from the group consisting of acute myocardial infarct, AMI, acute coronary syndrome, cardiac ischemia, ischemic heart disease, obstructive coronary artery disease, heart disease, compromised cardiac perfusion, heart failure, heart disease with or without ventricular tachycardia, angina pectoris, arrythmias, concussion to the heart, pulmonary hypertension affecting heart function, vascular heart disease due to endothelial damage or local inflammation or local infection, acute coronary syndrome, cardiac or myocardial ischemia, ischemic heart disease, and obstructive coronary artery disease.

In another embodiment of the invention, said CGRP compound is human.

In another embodiment of the invention, said CGRP compound is substituted, for example said CGRP compound may be substituted with polyethylene glycole (PEG) or said CGRP compound may be substituted with a molecular tag or, preferably a fluorescent marker such as 5(6)-carboxyfluorescein. The purpose of the substitutions is to increase the bulkyness of the CGRP compound.

In one embodiment of the invention, the CGRP compound for use as herein described, the compound is N-alpha-[2-(2-{2-[(S)-4-carboxy-4-(17-carboxyheptadecanoylamino)butyrylamino]ethoxy}ethoxy)acetyl][Ser1]alpha-human CGRP peptide.

In one embodiment of the invention, the CGRP compound for use as herein described, the compound is N-alpha-[2-(2-{2-[(S)-4-carboxy-4-(17-carboxyheptadecanoylamino)butyrylamino]ethoxy}ethoxy)acetyl][Ser1]beta-human CGRP peptide.

The compound for use as herein defined may be administered according to different routes. In one embodiment said compound is delivered by subcutaneous, intraperitoneal, or intravenous administration. In another embodiment, said compound is administered locally in the affected artery in connection with percutan coronar intervention (PCI) surgery.

Further, the compound for use is administered repeatedly. For example it is administered repeatedly after the first administration. The first administration may be, for example, after the PCI, or after the incident of AMI.

In an embodiment said CGRP compound for use as provided herein is delivered in combination with one or more compounds selected from the group consisting of beta blockers such as metoprolol, propranolol; RAS inhibitors such as ramipril, enalapril, captopril; AT1 blockers such as losartan, valsartan, candesartan; recombinant tissue plasminogen activators (TPA) such as alteplase, antithrombolytics such as aspirin, heparin, warfarin, clopidogrel; NOACs such as dabigatran, rivaroxaban; oxygen; nitroglycerin or opoids such as morphine.

In one embodiment the CGRP compound for use as provided herein, where the CGRP compound is administered at least once daily for one to thirty consecutive days immediately after incident.

In an embodiment, said CGRP compound for use as provided herein, is administered in an amount of between 0.01 to 1000 nanomole/kg body weight, preferably in an amount of between 0.1 to 1000 nanomole/kg body weight.

An aspect of the invention is a pharmaceutical composition comprising a CGRP compound, in combination with a pharmaceutically acceptable excipient, diluent or carrier.

Another aspect of the invention is a method of treatment of compromised organ perfusion, such as compromised myocardial perfusion, by endogenously inducing any CGRP family receptor with a larger CGRP:CGRP compound potency ratio in coronary artery than in mesenteric artery by administering a CGRP compound as defined herein.

DETAILED DESCRIPTION OF INVENTION

In particular, the present invention relates to calcitonin gene-related peptide (CGRP) compounds selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyryl-amino]-ethoxy}ethoxy)acetyl][Ser1]beta-human CGRP peptide (β-CGRP-analogue), or derivatives thereof, for use in inducing myocardial perfusion recovery, in connection with acute myocardial infarct, AMI.

The calcitonin gene-related peptide (CGRP) compound for use as identified herein is intended to be administered/used for endogenous mechanism.

The invention relates to new use of the calcitonin gene-related peptide (CGRP) compound selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyryl-amino]-ethoxy}ethoxy)acetyl][Ser1]beta-human CGRP peptide (β-CGRP-analogue). The CGRP compound of interest are those having an effect as bioactive CGRP receptor agonist which can cause a reduction in myocardial perfusion defect in experimental AMI (acute myocardial infarct) models upon administration once daily.

CGRP compounds may have differentiated effect on the coronary artery and the mesenteric artery. The CGRP compounds of interest herein are those CGRP compounds having a CGRP receptor agonist effect having a potency ratio (human CGRP $EC_{50}$: CGRP compound $EC_{50}$) larger in coronary artery than in mesenteric artery.

CGRP compounds of interest are presented in U.S. Pat. No. 8,835,379 B2.

More particular, the following compounds are of interest: Compound I: N-alpha-[2-(2-{2-[(S)-4-Carboxy-4-(17-carboxyheptadecanoylamino)-butyrylamino]-ethoxy}ethoxy)acetyl](Ser1]alpha-human CGRP peptide, according to formula I Formula I ing myocardial perfusion recovery, in connection with acute myocardial infarct, AMI, by activating any CGRP family of receptors with a larger CGRP:CGRP compound potency ratio in coronary artery than in mesenteric artery.

The present invention also relates to calcitonin gene-related peptide (CGRP) compounds selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino)butyryl-amino]-ethoxy}ethoxy)acetyl][Ser1]beta-human CGRP peptide (β-CGRP-analogue), or

```
                                            SEQ ID NO: 1
VTHRLAGLLSRSGGVVKNNFVPTNVGSKA
                                            SEQ ID NO: 2
DTAT
```

Compound II
N-alpha-[2-(2-{2-[(S)-4-Carboxy-4-(17-carboxyheptadecanoylamino)butyryl-amino]ethoxy}ethoxy)acetyl](Ser1]beta-human CGRP peptide, according to N-alpha-[2-(2-{2-[(S)-4-Carboxy-4-(17-carboxyheptadecanoylamino)butyryl-amino]ethoxy}ethoxy)acetyl](Ser1]alpha-human CGRP peptide, according to formula II Formula II

VTHRLAGLLSRSGGMVKSNFVPTNVGSKA    SEQ ID NO: 3

NTAT    SEQ ID NO: 4

With the compounds defined above are also CGRP compounds with conservative substitution included. Conservative substitution refers herein to a change in the amino acid composition of the protein in which a residue is replaced with a structurally similar substitute that does not substantially change the activity of the protein. A conservative substituted variant of a particular amino acid sequence referes to an amino acid substitution of an amino acid that is not critical for protein activity, or substitution of an amino acid with another amino acid having similar properties (for example, acidic, basic, positively or negatively charged, polar or non-polar, etc) such that the substitution of even critical amino acid do not substantially alter activity.

Conservative substitution tables providing functionally similar amino acids are well known in the art. The following six groups each contain amino acids that are conservative substitutions for one another: 1) alanine, serine, and threonine, 2) aspartic acid and glutamic acid, 3) asparagine and glutamine, 4) arginine and lysine, 5) isoleucine, leucine, methionine, and valine, and 6) phenylalanine, tyrosine, and tryptophan. One of skill in the art will appreciate that the above-identified substitutions are not the only possible conservative substitutions. For example, one may regard all charged amino acids as conservatice substitutions for each other whether they are positive or negative. In addition, individual substitutions, deletions, or additions which alter, add, or delete single amino acid or a small percentage of amino acids in an encoded sequence can also be "conservatively substituted variants".

Further, also pharmaceutically acceptable derivatives of the CGRP compounds herein defined are included in the invention. CGRP compounds I and II being further substituted are also to be included in the invention.

Pharmaceutically acceptable derivatives include salts and solvates of Compound I and II. Salts which may be mentioned include acid addition salts, ammonium salts, and N-oxides.

The compound for use as herein defined may be administered according to different routes. The administration route is selected to provide an exogenous administration of the compound in vivo, for example the compound is delivered by subcutaneous administration or intraperitoneal administration or intravenous administration. Said compound may also be administered locally in connection with percutan coronar intervention (PCI) surgery.

To achieve the desired effect, thus to preserve myocardial perfusion capacity, and by that improve survival after incident like acute myocardial infarct (AMI), the compound for use shall be administered at clinically relevant time point after the incident, for example one hour after the incident, followed with repeated administration during some time after. In particular, the CGRP compound is administered at least once daily for one to, for example, thirty consecutive days immediately after incident. Thus, the CGRP compound is for use in so-called subchronical treatment, between the first administration in connection with the AMI incidence and further administrations thereafter until the patient has been stabilized/recovered.

Further, the dose of the CGRP compound for use as defined herein is for example in an amount of between 0.01 to 1000, such as 0.1 to 1000, for example 0.1 to 100, nanomole/kg body weight.

The medicament comprising the CGRP compound is typically provided as an injectable solution, suitable for intravenous (i.v.), subcutaneous (s.c.) or intraperitoneal (i.p.) administration.

An aspect of the invention is a pharmaceutical composition comprising a CGRP compound, in combination with a pharmaceutically acceptable excipient, diluent or carrier.

As mentioned above, CGRP compounds and their mechanism are known previously. Even novel metabolically stable CGRP analogues and derivatives have been invented recently (U.S. Pat. No. 8,835,379 B2). It has been shown that these novel analogues have an effect to reverse the hypertension and complications of hypertension in experimental animals (Aubdool, A. A., P. Thakore, F. Argunhan, S. J. Smillie, M. Schnelle, S. Srivastava, K. M. Alawi, E. Wilde, J. Mitchell, K. Farrell-Dillon, D. A. Richards, G. Maltese, R. C. Siow, M. Nandi, J. E. Clark, A. M. Shah, A. Sams and S. D. Brain (2017). "A Novel alpha-Calcitonin Gene-Related Peptide Analogue Protects Against End-Organ Damage in Experimental Hypertension, Cardiac Hypertrophy and Heart Failure.").

Further, all previously known data indicate that the compounds of the present invention (Compound I and Compound II) and CGRP display similar pharmacological actions. However, the Compound I and Compound II as herein identified have been show to have in vitro potencies being approximately 10 times lower than that of CGRP (Sheykhzade, M., B. Abdolalizadeh, C. Koole, D. S. Pickering, K. Dreisig, S. E. Johansson, B. K. Abboud, R. Dreier, J. O. Berg, J. L. Jeppesen, P. M. Sexton, L. Edvinsson, D. Wootten and A. Sams (2018). "Vascular and molecular pharmacology of the metabolically stable CGRP analogue, SAX." Eur J Pharmacol; and Nilsson, C., T. K. Hansen, C. Rosenquist, B. Hartmann, J. T. Kodra, J. F. Lau, T. R. Clausen, K. Raun and A. Sams (2016). "Long acting analogue of the calcitonin gene-related peptide induces positive metabolic effects and secretion of the glucagon-like peptide-1." Eur J Pharmacol 773: 24-31. whereas the half-life and molecular size of Compound I is increased as compared to CGRP (Nilsson, Hansen et al. 2016).

A prolonged treatment with CGRP compounds causes cerebral vascular desensibilisation. Further, adminstration of CGRP may cause down-regulation of the receptors. With the invention, it has surprisingly been found that the CGRP compounds selected from N-alpha-[2-(2-{2-[(S)-4-carboxy-4-(17-carboxyheptadecanoylamino)-butyrylamino]ethoxy}ethoxy)acetyl][Ser1]alpha-human CGRP peptide (α-CGRP-analogue), or derivatives thereof; or N-alpha-[2-(2-{2-[(S)-4-carboxy-4-(17-carboxyheptadecanoylamino) butyryl-amino]-ethoxy}ethoxy)acetyl][Ser1]beta-human CGRP peptide (β-CGRP-analogue), or derivatives thereof, for use as herein defined are able to induce increased vascular CGRP sensitivity selectively in coronary artery. Therefore, the coronary arteries will specifically increase their vasodilatory response to repeated CGRP stimuli over time and specifically increase local perfusion.

Another advantage provided by the invention is that the CGRP compound for use according to the inventions may induce increased coronary artery CGRP receptor expression.

Another advantage provided by the invention is that the CGRP compound for use according to the inventions may induce endothelial protection.

In the following Example 2 it was aimed to compare the effect of CGRP and a metabolically stable CGRP analog, Compound I in peripheral (mesenteric), cerebral (basilar) and coronary (LAD) arteries to pursue the mechanism behind a novel and surprising finding of Compound I in AMI. All studies were conducted in artery segments from rats. It has been shown that the potency of Compound I is not lower in peripheral than coronary artery. Thus, a peripheral vasodilation will appear before a potential coronary dilation.

Compound I and CGRP induced vasodilation with comparable efficacy in all artery segment origins. However, in mesenteric and cerebral artery, the potency ratio (EC50 CGRP: EC50 Compound 1) was ~0.1-0.2 whereas the two vasodilators were equipotent in coronary artery segments (potency ratio of ~1). It was evident that the CGRP potency was 10 fold lower in coronary artery than mesenteric and basilar and thus, the reason for an equipotent coronary effect of Compound I and CGRP was rather a reduction of CGRP potency than an induction of Compound I potency. The reduced CGRP potency may depend on reduced stability of native CGRP in coronary specimens; increased perivascular uptake of CGRP but not Compound I in coronary specimens; or that increased endogenous CGRP is released during preconstriction of basilar and mesenteric (but not coronary artery) resulting in an overestimated potency of externally applied CGRP.

Further, it is also found that the potency of Compound I and CGRP is similar in isolated coronary artery segments. This finding is novel and surprising since the in vitro potency of Compound I is 10 fold lower than that of CGRP in all vascular and cellular evaluations published so far.

Here we demonstrate CGRP-sensibilization specifically in coronary LAD segments after repeated CGRP-receptor stimulation or artery culture.

Neither culture nor repeated CGRP-agonist dosing showed significant CGRP-agonist sensibilization in mesenteric artery. This indicates that CGRP-sensibilization is specific for coronary artery and thereby provides a possible explanation for the surprising cardioprotective effect of Compound I in acute myocardial infarction. It has previously been shown that CGRP receptors are desensibilized after repeated stimuli, however, there is no previous examples of CGRP-sensibilization. This is further shown in Example 3.

EXAMPLES

By way of examples, and not limitation, the following examples identify CGRP compounds for use pursuant to embodiments of the present invention.

Example 1—Effect of a CGRP-Analogue in Acute Myocardial Infarction (Permanent LAD (Left Anterior Descending Artery) Occlusion)

Materials and Methods

Figure 1:
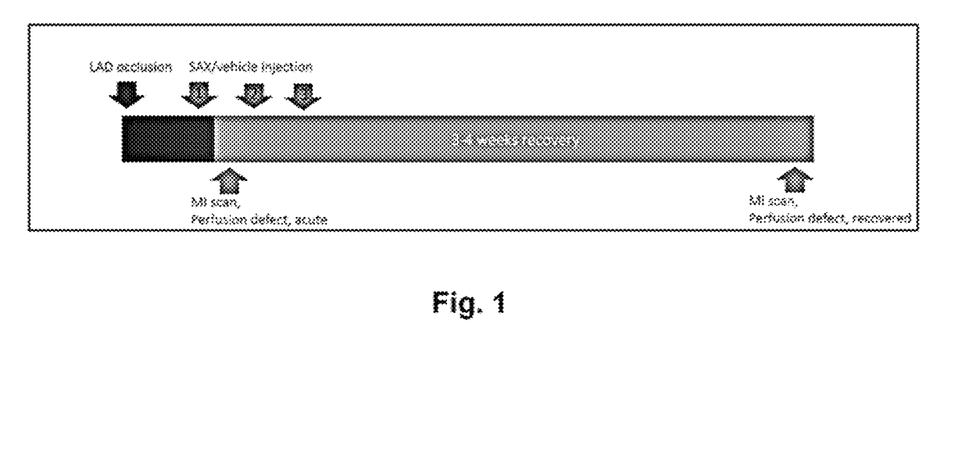
FIG. 1 Experimental study design.
Figure 2:
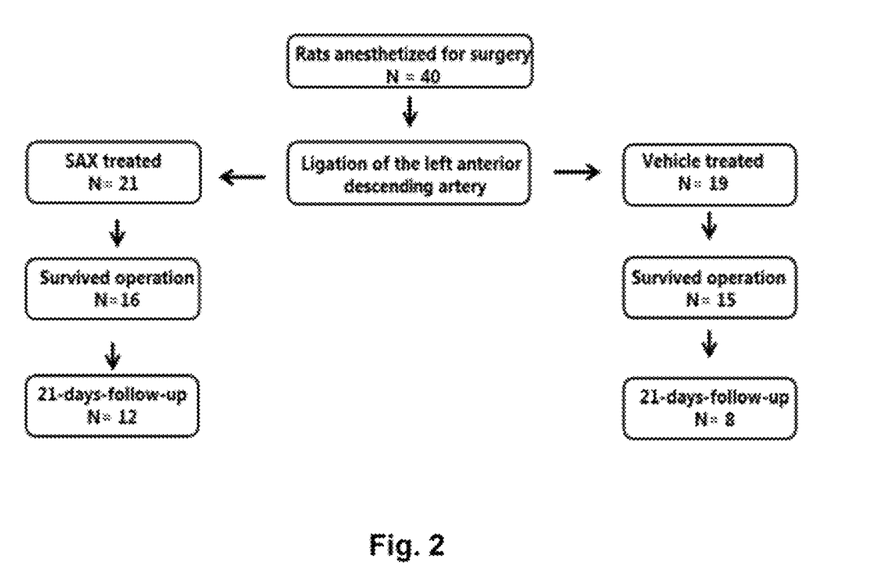
FIG. 2. Overview of experimental animals.

Experimental myocardial infarction is induced by LAD ligation in rats. Size of the acute myocardial perfusion defect is determined by myocardial perfusion imaging using SPECT/CT. The animals were subsequently treated with 3 doses of Compound I or vehicle during the first 48 hours of the 3 weeks recovery phase. All surviving rats underwent follow-up myocardial perfusion imaging using SPECT/CT 21 days after the infarct to determine the final infarct size. The design is outlined in FIG. 1.

For SPECT detection of the acute and delayed perfusion defect we essentially used a previously described method, carefully compared to the classical method (TTC (triphenyltetrazolium chloride) staining) for post occlusion coronary infarct size (Acton, Thomas et al. 2006).

Drugs and Formulations

The CGRP analogue, Compound I, was synthesised (>84% purity), stored and formulated as previously described (Nilsson, Hansen et al. 2016).

Rat Model of Acute Myocardial Infarction (AMI)

All animal experiments were approved by the Danish Animal Experiments Inspectorate (Permit nr. 2016-15-0201-00920). The animals were cared for at a core animal facility at 21±2° C. with a 12:12 hours dark:light cycle, and had access to water and standard rodent chow ad libitum. The animals were acclimatized 7-12 days before inclusion in the experiment.

AMI surgery was conducted using the procedure for permanent LAD occlusion. A total of 40 male Sprague-Dawley rats (8 weeks, Charles River) were randomly divided into two groups and treated with Compound I (21 animals) or vehicle (19 animals) immediately after surgery.

The rats were anaesthetized with 4% sevoflurane. Rats were intubated and ventilated (UNO micor-ventilator-O3, Netherlands) and maintained anaesthetized with sevuflorane 2.5% to 4%. Rats were placed on a heated surface during surgery. In the rat's tail vein a 24G intravenous catheter was placed (Vasofix® Safety, Braun, Denmark). Before incision the rats were pain treated subcutaneously with Buprenorphine 0.05 mg/kg. After surgery the rats were paintreated four times the first 24 hours and three times the next 24-72 hours.

After insuring sterile surgical conditions, an incision was made in the skin and a thoracotomy was performed. This was placed at either the third or fourth intercostal space depending on size. The pericardium was identified and opened. After inspection of the heart, the LAD was identified and ligated caudal of its origin with a 5-0 polypropylene suture. The myocardium was visually observed for ischemia. If there was no discoloration of the myocardium, another suture was made until ischemia was confirmed by discoloration of the myocardium. One minute after ligation, the rats were injected intravenously with 99-technetium sestamibi to determine the acute perfusion defect. After injection of sestamibi, suture type vicryl 4-0 was used to close the thoracotomy, muscle layer and skin. 20 minutes after injections with sestamibi, 100 nmol/kg of Compound I or vehicle was administered intraperitoneal. This time window allowed the sestamibi to be trapped into the myocyte before any potential influence of Compound I. Two additional Compound I or vehicle doses were given subcutaneously 24 and 48 hours after surgery. Six (29%) rats in the Compound I treated group and 7 (35%) in the vehicle treated group died after the first treatment but before SPECT scan leaving 15 rats treated with Compound I and 12 rats treated with vehicle prior to determination of an acute perfusion defect size. During the 21-days follow-up period a further 3 rats in the Compound I group (14%) and 4 (20%) in the vehicle treated group died, leaving a total of 12 rats treated with Compound I and 8 vehicle rats for assessment of both acute and follow-up perfusion defect.

Myocardial Perfusion Imaging

Rats underwent single photon emission computer tomography (SPECT) on the day of the surgery and 21 days post-surgery to determine acute and final perfusion defect size. Imaging was performed on a preclinical SPECT/CT scanner (Mediso Nanoscan, Hungary). The rats were anesthetized with sevuflorane 4% for SPECT-scan to be obtained. On the day of the surgery, the rats were perioperatively injected with 99-technetium Sestamibi (median 106 mBq [99; 116]) as described above. On the 21-days follow-up the rats were anesthetized with sevoflurane 4%. In the rat's tail vein an 24G intravenous catheter was placed (Vasofix® Safety, Braun, Denmark). After the catheter was placed, the rats were injected with 99-tecnetium (median 122 [106; 129]).

For the scan, the rats were placed in special bed, provided by the vendor, in a prone position. The rats were monitored with ECG, respiration and temperature. A scout CT imaging was performed to ensure correct position of the SPECT-detectors field of view over the heart. One hour after injection of sestamibi, the SPECT acquisition was initiated. Scan time was between 20 and 40 minutes, depending on injected activity, adjusted to ensure number of counts above 100000 counts/frame/detector. For attenuation correction and anatomical co-registration, CT scan was acquired after the SPECT. All images were reconstructed using vendor software (Mediso Nanoscan, Hungary) using recommended parameters.

SPECT Image Analysis

Corridor4DM version 2017 (Invia LLC, USA) was used for semi-automatic analyses of the SPECT data. The SPECT images were automatically oriented into short, vertical and horizontal long axis. The myocardial contour was then determined automatically. Both reorientation and contouring were visually inspected and corrected by the experienced investigators in conjunction. Baseline and 3 week-follow up images were analyzed simultaneously to ensure correct reorientation. The two investigators were blinded to treatment during this process. The perfusion was quantified as local myocardial 99-technetium sestamibi activity normalized to maximum myocardial activity equivalent to normal clinical human standard. Each scan was compared to a normal rat database (produced at our side using the same species of rats and the same imaging parameters in 20 rats), to assess the perfusion compared to a normal distribution. These values were obtained in myocardial segments according to the 17 American Heart Association (AHA) segments model. The perfusion in each segment was automatically graded from 0 (normal perfusion) to 4 (absent perfusion). The total perfusion of the heart was summed from each segment in "summed rest score" (SRS). The maximal SRS is 68 (4×17 segments) corresponding to 100% left ventricular perfusion defect and the minimal score is 0, corresponding to a normally perfused left ventricle. Individual acute perfusion defect is given by SRS0 and the perfusion defect after 21 days of recovery, SRS21.

Data Analysis and Statistics

Absolute perfusion defect is represented by the individual SRS value and the absolute perfusion recovery is given by SRS21−SRS0.

% acute perfusion defect is given as (SRS0/SRSmax)*100 where SRS0 represents the acute SRS value and SRSmax is 68.

% recovery is given as (SRS21−SRS0/SRSmax)*100, where SRS21 represents the SRS value after 21 days of recovery.

Differences in average 'SRS perfusion defect' were evaluated using unpaired non-parametric t-test (GraphPad Prism) and differences in % acute perfusion defect and % perfusion recovery were evaluated using unpaired parametric t-tests. Significance was considered when P-values <0.05 was obtained.

Results

The experimental and physiological characteristics of Compound I and vehicle-treated animals is given in table 1.

TABLE 1

Experimental data are given in median [interquartile range, IQR]. For comparison, the non-parametric Mann-Whitney Test was used. A two-sided P value < 0.05 was considered significant.

| Baseline | Compound I | Vehicle | P |
|---|---|---|---|
| Rat, n | 21 | 19 | |
| Weight, grams | 281 [258; 306] | 360 [277; 390] | 0.015 |
| Number of ligature | 1 [1; 2] | 1 [1; 2] | 0.37 |
| Time from ligation to $^{99}$Tc-injection, minute | 1 [1; 2.5] | 1 [1; 4] | 0.95 |
| Time from ligation to intervention, minute | 21 [20; 21] | 21 [20; 22] | |

TABLE 1-continued

Experimental data are given in median [interquartile range, IQR]. For comparison, the non-parametric Mann-Whitney Test was used. A two-sided P value < 0.05 was considered significant.

| Baseline | Compound I | Vehicle | P |
|---|---|---|---|
| Number of rats which survived operation | 16 | 15 | |
| Time from $^{99}$Tc-injection to SPECT-scan, minute | 68 [59; 163] | 61 [59; 76] | 0.23 |
| $^{99}$Tc injected, MBq | 109 [94; 120] | 106 [102; 116] | 0.83 |
| Rats, n at 3 weeks follow up | 12 | 8 | |
| Weight, grams | 406 [364; 422] | 446 [414; 459] | 0.11 |
| Time from $^{99}$Tc-injection to SPECT-scan, minute | 70 [56; 223] | 66 [60; 70] | 0.62 |
| $^{99}$Tc injected, MBq | 111 [99; 123] | 127 [122; 139] | 0.007 |

TABLE 2

Acute perfusion defect and recovery of perfusion defect in all completers and in a subgroup with <15% acute perfusion defect. Data are represented in absolute SRS values and in %, given as mean ± SEM. The differences in absolute SRS values were evaluated using the non-parametric Mann Whittney Test and significance considered when P < 0.05. Differences in relative acute perfusion defect and relative recovery was analysed using a parametric non-paired t-test.

| | Compound I | Vehicle | P |
|---|---|---|---|
| | All animals completing the study | | |
| Number of animals completing the study | 12:16 (75%) | 8:15 (53%) | |
| Number of animals dying before 2. SPECT scan | 4:16 (25%) | 7:15 (47%) | |
| Acute perfusion defect, % | 21.2 ± 3.9 | 12.5 ± 3.7 | 0.1412 |
| Acute perfusion defect, SRS | 14.4 ± 2.6 | 8.5 ± 2.5 | 0.1290 |
| Perfusion recovery, % | 55.1 ± 6.4 | 10.5 ± 25 | 0.0546 |
| Perfusion recovery, SRS | 6.5 ± 1 | 2 ± 2 | 0.0398 |
| Number of animals in subgroup (acute perfusion defect < 15%) | 6 | 6 | |
| Acute defect in subgroup, % | 9.8 ± 2.0 | 7.8 ± 1.2 | 0.4188 |
| Acute defect in subgroup, SRS | 6.7 ± 1.3 | 5.3 ± 0.8 | 0.3312 |
| Perfusion recovery in subgroup, % | 66.2 ± 9.0 | −3.7 ± 31.8 | 0.0389 |
| Perfusion recovery in subgroup, SRS | 3.8 ± 0.6 | −0.5 ± 1.2 | 0.0087 |

Figure 3:
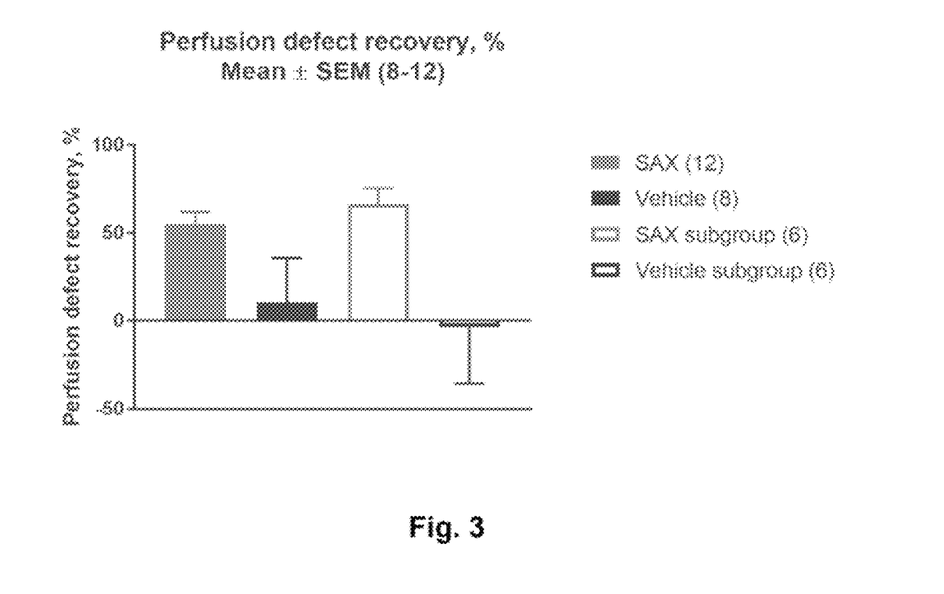
FIG. 3. Perfusion defect recovery in Compound I and vehicle-treated animals. The two first bars represent all completing animals and the latter represents subgroups of individual animals with <15% acute perfusion defect. Data is given as mean±SEM (n) and corresponding values and statistical analysis is shown in table 2. (Compound I is denoted SAX in the figures)
Figure 4:
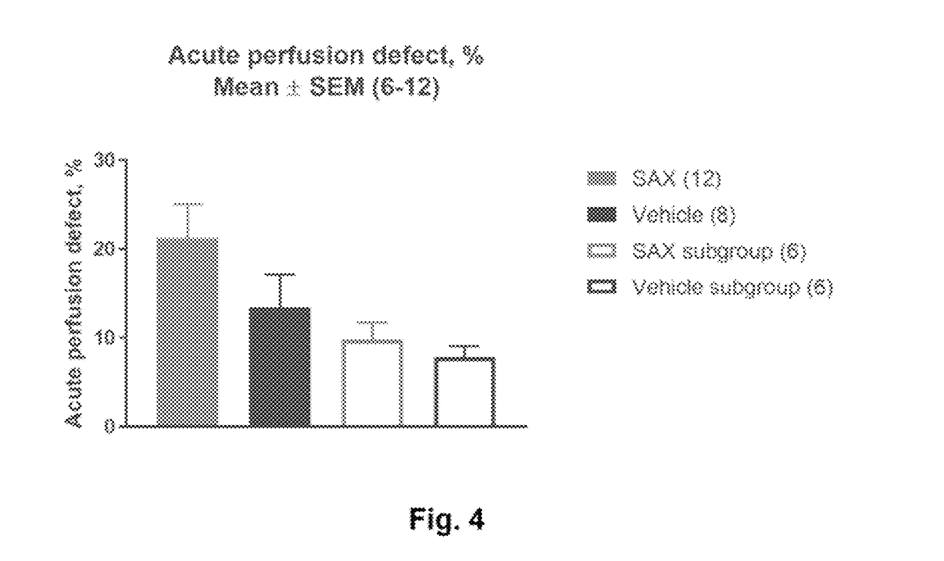
FIG. 4. Acute perfusion defect in Compound I and vehicle-treated animals. The two first bars represent all completing animals and the latter represents subgroups of individual animals with <15% acute perfusion defect. Data is given as mean±SEM (n) and corresponding values and statistical analysis is shown in table 2.

Twelve of the 16 Compound I treated animals (75%) and 8 of 15 vehicle treated (53%) animals survived the surgery and the 3 weeks recovery period. The relative perfusion defect recovery (%) was 55.1±6.6 and 10.5±25 in Compound I and vehicle treated animals, respectively (FIG. 3 and table 2). In absolute SRS values, the difference between Compound I treated and vehicle treated animals was significant (P<0.05). Although not significant, a tendency towards a lower initial perfusion damage is seen in the vehicle group (FIG. 4). However, analyzing subgroups of animals with <15% acute perfusion defect eliminated the bias (FIG. 4 and table 2) and relived a larger difference in perfusion defect in Compound I and vehicle-treated animals (FIG. 3 and table 2).

In groups of completing animals (n=8-12) and in subgroups (n=6) the difference between absolute perfusion defect recovery was significant (table 2). The difference in relative perfusion defect recovery was significant in subgroups whereas a p-value of 0.0546 was reached when comparing groups of all completing animals. Taken together, we conclude that Compound I treatment for 3 successive days after experimental AMI induce a large improvement of myocardial perfusion recovery during the 3 weeks.

The study design and number of completing animals in the current study does not allow us to conclude on whether the observed increased survival rate in Compound I treated rats was significant (75 vs 53%). However, the notion of reduced survival rate in vehicle treated animals and the corresponding reduced acute perfusion defect supports the notion, that Compound I-treated animals display robustness towards experimental AMI and induced recovery capacity.

It can be concluded that there is a tendency (not statistically significant) towards an increased survival rate in Compound I treated AMI rats. Further, a significant improved recovery of perfusion defect is seen one month after the AMI if associated with 3 days of Compound I treatment.

Example 2—Effect of α-CGRP Compound in Cerebral, Peripheral and LAD Artery

Materials and Methods
Drugs and Chemicals

The CGRP analogue, Compound I, was synthesised (>84% purity), stored and formulated as previously described (Nilsson, Hansen et al. 2016).

Vasoactive substances, $PGF_{2\alpha}$ (Dinolytic Vet., 5 mg/ml dinoprost, Pfizer) and human αCGRP (Bachem H-1470) were dissolved in water, aliquoted and stored at −20° C. until use.

Physiological salt solution (PSS) used for in vitro vascular studies had the following composition (in mM): NaCl 119, $NaHCO_3$ 25, KCl 4.7, $NaH_2PO_4$ 1.18, $MgSO_4 \cdot 7H_2O$ 1.17, $CaCl_2$ 1.5, ethylenediaminetetraacetic acid (EDTA) 0.0027 and glucose 5.5 with pH adjusted to 7.4. Potassium enriched PSS (KPSS) was prepared by replacing all sodium chloride with an equimolar amount of potassium chloride, which obtained a final $K^+$ concentration of 125 mM. All buffers were aerated with 5% $CO_2$/95% $O_2$ to maintain pH 7.4.

Animals

All animal procedures were carried out in accordance and compliance with all national laws and guidelines. Male Sprague-Dawley rats (250-350 g) (Taconic, Ejby, Denmark) were housed in the local animal facility in a temperature (22-23° C.)—and humidity-controlled environment with 12 h light and 12 h dark cycle and adlibitum access to standard chow and water. Rats were sedated with $CO_2$ and euthanized by guillotining followed by exsanguination.

Vasomotor Effects of Isolated Artery Segment

Basilar, mesenteric and coronary arteries were isolated immediately and ring artery segments were stored in ice cold PSS buffer before being mounted on 40 μm stainless steel wires in a Multi Wire Myograph System organ bath (model 610M, Danish Myo Technology A/S, Denmark). Each segment was immersed in 37° C. PSS solution, continuously aerated with 5% $CO_2$/95% $O_2$ to maintain pH 7.4. The buffer was continuously aerated with oxygen enriched with 5% $CO_2$ resulting in a pH of 7.4. One wire was connected to a micrometer screw enabling adjustments of the distance between the wires. The other wire was connected to a force displacement transducer attached to an analogue-digital converter unit (ADInstruments, Chalgrove, UK).

Measurements of vascular tone were recorded using the data acquisition hardware Power Lab unit (ADInstruments). To ensure optimal conditions for maximal force development, each artery segment was carefully stretched to 90% of the internal circumference that the vessel would have under the passive transmural pressure of 100 mm Hg. Following an equilibration period of approximately 20 min, each segment was exposed twice to KPSS to confirm smooth muscle cell viability and the reproducibility of depolarization-induced contractions.

After 15 min equilibration, a stable precontraction tone (50-80% of the KPSS-induced steady state contraction) was induced in arterial segments by $PGF_{2\alpha}$ (3-10 μM). The segments were then subject to cumulative applications of CGRP or Compound I (30 μM-300 nM).

Concentration-dependent vasodilatory responses of artery segments were normalized as percentage of precontraction remaining.

Data Analysis and Statistics

Vasodilation is expressed as percentage of the remaining precontraction tone induced by $PGF_{2\alpha}$. Vessel wall tension=Force/(vessel wall length), where vessel wall length=2×segment length. Active tension was determined by subtracting the passive tension (resting tension in PSS) from the total tension (during KPSS or $PGF_{2\alpha}$ challenge).

All pharmacological data were analysed using Prism 7.02 (GraphPad Software Inc., San Diego, CA) and given as mean±S.E.M. For all analyses, the data were unweighted and each y value (mean of replicates for each individual experiment) was considered an individual point. All concentration-response data were analysed with a three-parameter logistic equation as described previously:

$$Y=Bottom+(Top-Bottom)/(1+10^{((Log\ IC50-Log[A]*nH))})$$

where Bottom represents the y value in the absence of ligand(s), Top represents maximal stimulation in the presence of ligand(s), [A] is the molar concentration of agonist and $EC_{50}$ is the molar concentration of ligand required to generate a response halfway between Top and Bottom and nH is the Hill slope (constrained to 1). $EC_{50}$ is defined as the compounds potency.

Differences in $pEC_{50}$ and Emax values were analysed with paired (animal) t-tests and considered significant as $P<0.05$. Potency ratios ($EC_{50}$ CGRP: $EC_{50}$ Compound 1) were determined individually for coronary, cerebral and mesenteric artery and the corresponding $pEC_{50}$ values were used for statistical evaluation of differences.

Results

Figure 5:
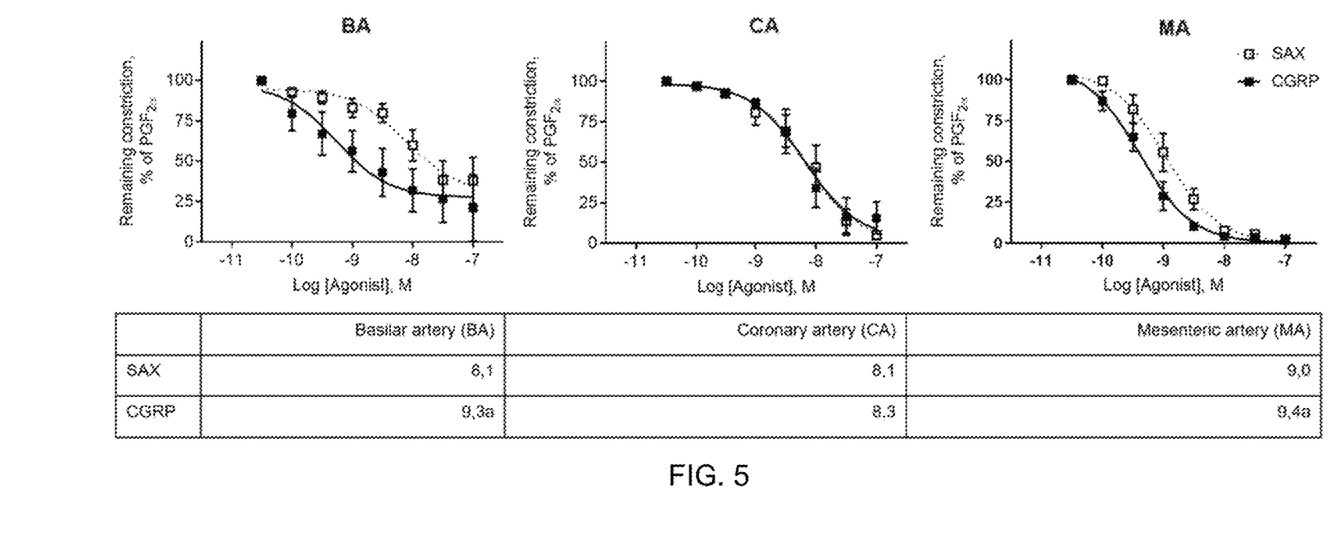
FIG. 5. Dose response curves of Compound I and CGRP in isolated segments of cerebral (basilar, BA), coronary (left anterior descending artery (LAD), CA) and peripheral (mesenteric, MA) artery. The negative logarithme of the molar potencies ($pEC_{50}$) values are given below the curves and significant differences between $pEC_{50}$-values in coronary artery and other artery sources are given by a, indicating p-values below 0.05. Number of independent paired (animal) experiments are 6.

The vasodilatory effect of Compound I and CGRP for each specific concentration gives individual dose-response curves in basilar, mesenteric and coronary artery (FIG. 5). Compound I and CGRP induced vasodilation with comparable efficacy in all artery segment origins. However, in mesenteric and cerebral artery, the potency difference between CGRP and Compound I was 5-10-fold whereas the two vasodilators were equipotent in coronary artery segments. It was evident that the CGRP potency was 10 fold lower in coronary artery than mesenteric and basilar and thus, the reason of an equipotent coronary effect of Compound I and CGRP was rather a reduction of CGRP potency than an induction of COMPOUND I potency. In all tissues and cells examined so far, CGRP has consistently been approximately 10 fold more potent than Compound I. This means that we generally need a ten-fold higher molar concentration of Compound I than of CGRP to induce an identical biological response to naturally occurring cells, recombinant CGRP receptor expressing cell lines and to isolated segment of artery. The isolated left anterior descending (LAD) branch of the rat coronary artery is the first tissue identified where CGRP and Compound I is equipotent. Thus, in isolated rat LAD an identical molar concentration of CGRP and Compound I induced identical amount of vasodilation. It was evident that the CGRP potency was 10 fold lower in coronary artery than mesenteric and basilar and thus, the reason of an equipotent coronary effect of Compound I and CGRP was rather an apparent reduction of CGRP potency than an induction of COMPOUND I potency. The reason for the reduced in vitro CGRP-potency in isolated LAD might be functional depletion of CGRP in this specific tissue.

Thus, the pharmacological profile of Compound I is different from that of CGRP selectively in coronary LAD artery. The reason for reduced CGRP potency is speculative but might be one of the following: reduced stability of native CGRP in coronary specimens; increased perivascular uptake of CGRP but not Compound I in coronary specimens or that increased endogenous CGRP is released during preconstriction of basilar and mesenteric but not coronary artery) resulting in an overestimated potency of externally applied CGRP.

It can be concluded that the vasodilatory potency of Compound I is lower than that of CGRP in mesenteric and basilar artery whereas the potency of Compound I and CGRP is similar in coronary artery.

Example 3—CGRP-Agonist Sensibilization in Coronary LAD

Materials and Methods

All experiments were conducted as described in Example 2 with the following modifications:

Effect of repeated dose-response: A second cumulative dose-response curves were conducted 90-120 minutes after completion of the first COMPOUND I or CGRP dose-response curve.

Effect of artery culture: After dissection, artery segments were cultured (DMEM supplemented with penicillin and streptomycin) for 24 h at 37° C.±Compound I (10 nM) for 24 h. Artery segments were divided for comparison of the effect of Compound I and CGRP in fresh and cultured artery segments, respectively.

Results

Sensitization in Coronary LAD Artery

Figure 6:
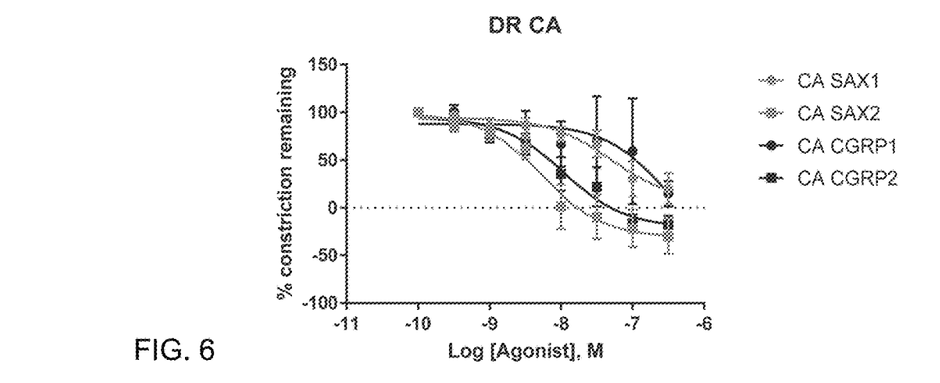
FIG. 6. Repeated dose response curves with Compound I and CGRP in coronary LAD artery segments. At each concentration of CGRP or Compound I, data are given as mean±SEM for 6 individual artery segments from 6 animals.

As seen in Example 2 the potency and efficacy of CGRP and Compound I are not different in isolated segments of coronary LAD artery (FIG. 6). Repeating the cumulative stimulation with Compound I or CGRP does not change the potency ratio, however, it induces a shift in potency towards significant sensitization.

Figure 7:
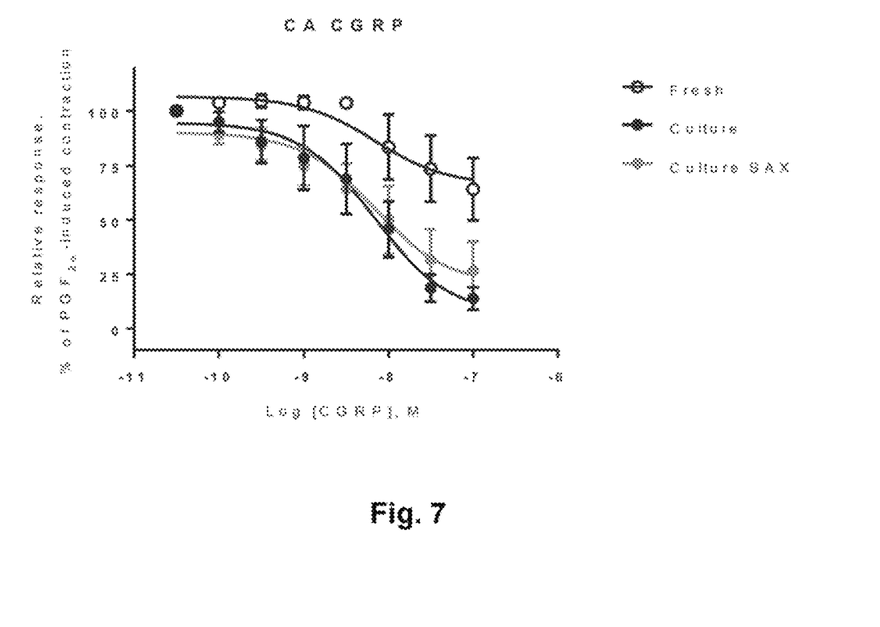
FIG. 7. Dose response curves with CGRP in fresh and cultured coronary LAD artery segments. At each concentration of CGRP, data are given as mean±SEM for 6 individual artery segments from 6 animals.

Artery culture in the absence and presence of 10 nM Compound I also induce sensibilization of CGRP-agonist-induced vasodilation (FIG. 7).

No Sensitization in Mesenteric Artery

Figure 8:
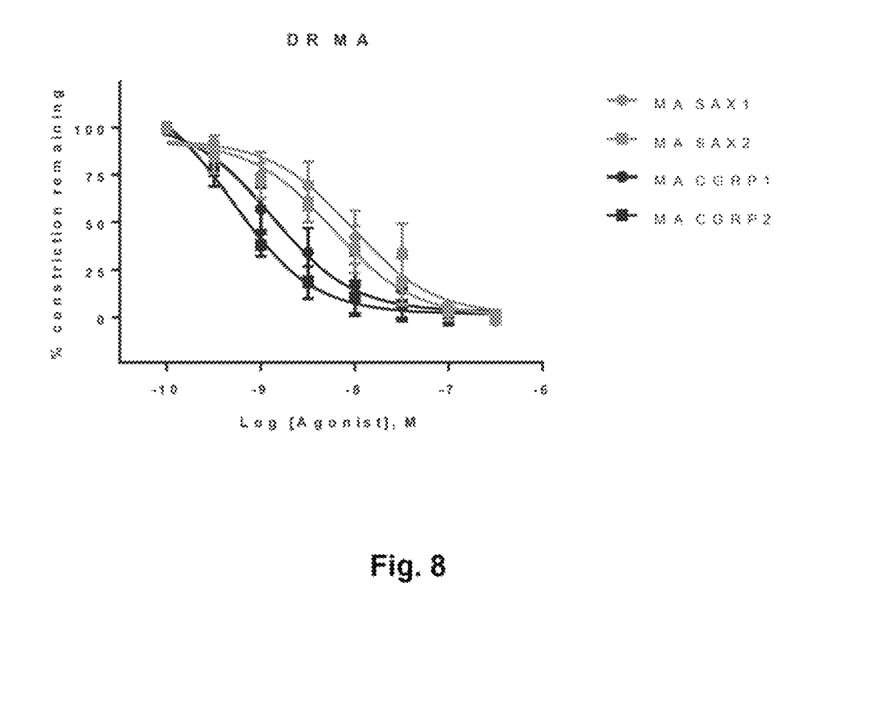
FIG. 8. Repeated dose response curves with Compound I and CGRP in mesenteric artery. At each concentration of CGRP or Compound I, data are given as mean±SEM for 6 individual artery segments from 6 animals.
Figure 9:
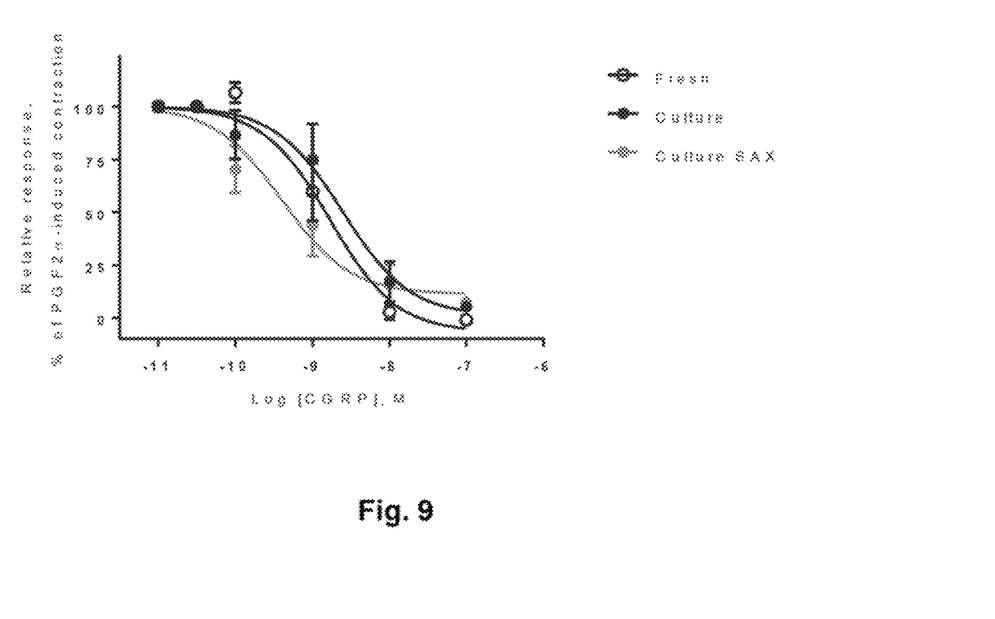
FIG. 9. Dose response curves with CGRP in fresh and cultured coronary LAD artery segments. At each concentration of CGRP, data are given as mean±SEM for 7 individual artery segments from 7 animals.

In isolated mesenteric artery, no CGRP-agonist-induced CGRP sensibilization was seen (FIGS. 8 and 9). Further, the potency ratio between Compound I and CGRP is maintained (FIG. 8).

CONCLUSION

Culture and CGRP-agonistic stimulation of coronary LAD segments induce CGRP sensitization. The phenomenon of induced CGRP-agonist sensitization is novel. So far, only CGRP-desensitization has been found. The similar potency of Compound I and CGRP in coronary artery supports previous findings and might be caused by increased coronary artery CGRP degradation or by LAD specific receptor distribution.

While the invention has been described in connection with what is presently considered to be the most practical embodiments, it is to be understood that the invention is not to be limited to the disclosed embodiments, but On the ccntfary, it is intended to cover various modifications and equivalents included within the spirit and scope, of the description.

The invention claimed is:

1. A method for the treatment of acute myocardial infarction (AMI), the method comprising:
   administering a calcitonin gene-related peptide (CGRP) compound,
   wherein the CGRP compound is N-alpha-[2-(2-{2-[(S)]-4-carboxy-4-(17-carboxyheptadecanoylamino)-butyryl-amino]-ethoxy}ethoxy)acetyl][Ser1]beta-human CGRP peptide (β-CGRP-analogue), and a pharmaceutically acceptable salts and solvates thereof,
   wherein the CGRP compound is administered at least once per day, and
   wherein the CGRP is administered for one to thirty consecutive days immediately after incident.

2. The method for treatment according to claim 1, wherein said CGRP compound is human.

3. The method for treatment according to claim 1, wherein said CGRP compound is substituted.

4. The method for treatment according to claim 3, wherein said CGRP compound comprises polyethylene glycole (PEG).

5. The method for treatment according to claim 3, wherein said CGRP compound comprises a biomarker.

6. The method for treatment according to claim 1, wherein said CGRP compound is delivered in combination with one or more compounds selected from the group consisting of a beta blocker, a renin-angiotensin-system (RAS) inhibitor, an angiotensin 1 (AT1) blocker, a recombinant tissue plasminogen activator (TPA), an antithrombolytic, a new oral anticoagulant (NOAC), and an opioid,
   wherein the beta blocker is metoprolol or propranolol,
   wherein the RAS inhibitor is ramipril, enalapril, or captopril,
   wherein the AT1 blocker is losartan, valsartan, or candesartan,
   wherein the recombinant TPA is alteplase,
   wherein the antithrombolytic is aspirin, heparin, warfarin, or clopidogrel,
   wherein the NOAC is dabigatran, rivaroxaban, oxygen, or nitroglycerin, and
   wherein the opioid is morphine.

7. The method for treatment according to claim 1, wherein said CGRP compound is delivered by subcutaneous, intraperitoneal, or intravenous administration.

8. The method for treatment according to claim 1, wherein said CGRP compound is administered locally in connection with percutan coronar intervention (PCI).

9. The method for treatment according to claim 1, wherein said CGRP compound is administered in connection with an incident of AMI.

10. The method for treatment according to claim 9, wherein said CGRP compound is administered within one hour after the AMI incident.

11. The method for treatment according to claim 1, wherein the CGRP compound is administered repeatedly.

12. The method for treatment according to claim 1, wherein the CGRP compound is administered in an amount of between 0.01 to 1000 nanomole/kg body weight.

13. The method for treatment according to claim 5, wherein the biomarker is a fluorescent marker.

14. The method of treatment according to claim 1, wherein said CGRP compound induces myocardial perfusion recovery in connection with AMI.

15. The method of treatment according to claim 14, wherein said CGRP compound induces myocardial perfusion recovery by activating any CGRP family of receptors with a larger CGRP:CGRP compound potency ratio in coronary artery than in mesenteric artery.

* * * * *

SEQUENCE LISTING

```
<160> NUMBER OF SEQ ID NOS: 4

<210> SEQ ID NO 1
<211> LENGTH: 29
<212> TYPE: PRT
<213> ORGANISM: Artificial Sequence
<220> FEATURE:
<223> OTHER INFORMATION: Peptide sequence in formula I

<400> SEQUENCE: 1

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala
            20                  25

<210> SEQ ID NO 2
<211> LENGTH: 4
<212> TYPE: PRT
<213> ORGANISM: Artificial Sequence
<220> FEATURE:
<223> OTHER INFORMATION: Peptide sequence in formula I

<400> SEQUENCE: 2

Asp Thr Ala Thr
1

<210> SEQ ID NO 3
<211> LENGTH: 29
<212> TYPE: PRT
<213> ORGANISM: Artificial Sequence
<220> FEATURE:
<223> OTHER INFORMATION: Peptide sequence present in fomula II

<400> SEQUENCE: 3

Val Thr His Arg Leu Ala Gly Leu Leu Ser Arg Ser Gly Gly Met Val
1               5                   10                  15

Lys Ser Asn Phe Val Pro Thr Asn Val Gly Ser Lys Ala
            20                  25

<210> SEQ ID NO 4
<211> LENGTH: 4
<212> TYPE: PRT
<213> ORGANISM: Artificial Sequence
<220> FEATURE:
<223> OTHER INFORMATION: Peptide sequence in formula II

<400> SEQUENCE: 4

Asn Thr Ala Thr
1
```